United States Patent [19]

Meybeck et al.

[11] Patent Number: 5,505,934
[45] Date of Patent: Apr. 9, 1996

[54] COSMETIC OR PHARMACEUTICAL COMPOSITION CONTAINING AN EXTRACT OF COLEUS ESQUIROLII, COLEUS SCUTELLARIOIDES OR COLEUS XANTHANTHUS

[75] Inventors: Alain Meybeck; Frédéric Bonte, both of Courbevoie; Marc Dumas, Colombes, all of France

[73] Assignee: L.V.M.H. Recherche, Colombes, France

[21] Appl. No.: 199,303

[22] PCT Filed: Sep. 4, 1991

[86] PCT No.: PCT/FR91/00706

§ 371 Date: Jul. 15, 1994

§ 102(e) Date: Jul. 15, 1994

[87] PCT Pub. No.: WO93/04667

PCT Pub. Date: Mar. 18, 1993

[51] Int. Cl.⁶ .................................................. A61K 7/42
[52] U.S. Cl. ........................ 424/59; 424/74; 424/195.1
[58] Field of Search ................................. 424/195.1, 74, 424/59

[56] References Cited

U.S. PATENT DOCUMENTS

| | | | |
|---|---|---|---|
| 4,088,659 | 5/1978 | Bhat | 260/345.2 |
| 4,453,941 | 6/1984 | Jacobs | 8/424 |
| 4,931,066 | 6/1990 | Grollier | 8/410 |
| 5,017,368 | 5/1991 | Sugiyama | 424/70 |
| 5,078,989 | 1/1992 | Ando | 424/62 |

Primary Examiner—C. Warren Ivy
Assistant Examiner—Evelyn Huang
Attorney, Agent, or Firm—Popham, Haik, Schnobrich & Kaufman, Ltd.

[57] ABSTRACT

The invention relates to cosmetic or pharmaceutical, particularly dermatological, compositions. More particularly, the invention relates to the utilization of an extract of Coleus Esquirolii, Coleus Scutellariodes or Coleus Xanthanthus or one of the mixtures thereof for the preparation of cosmetic or pharmaceutical, particularly dermatological, composition. In particular, the invention helps to efficiently promote skin or hair pigmentation.

23 Claims, No Drawings

COSMETIC OR PHARMACEUTICAL COMPOSITION CONTAINING AN EXTRACT OF COLEUS ESQUIROLII, COLEUS SCUTELLARIOIDES OR COLEUS XANTHANTHUS

This application is (the National Phase) of the PCT/FR91/00706, filed on Sep. 4, 1991.

The present invention relates essentially to a cosmetic or pharmaceutical composition, especially dermatological composition, containing an extract of *Coleus esquirolii, Coleus scutellarioides* or *Coleus xanthanthus,* intended in particular for promoting the pigmentation of the skin or hair, and to the process for its preparation.

It further relates to the use of an extract of *Coleus esquirolii, Coleus scutellarioides* or *Coleus xanthanthus* for the preparation of such a cosmetic or pharmaceutical composition.

The Coleus species belong to the family of the Labiatae, as do the very closely related Plectranthus species, and are often confused with one another since they generally also originate from the same regions. Thus the species *Coleus barbatus* is generally designated by the name *Plectranthus barbatus*, and the species *Coleus aromaticus* has the alternative name *Plectranthus aromaticus*. There are nearly 200 species of Coleus in existence, spread throughout the tropical and subtropical regions of Asia, Africa, Australia and the Pacific islands. About 9 species are indexed in India. The 10 principal varieties of Coleus are indexed in the Indian dictionaries, in particular "The Wealth of India, a Dictionary of Indian Raw Materials and Industrial Products, Raw Materials", volume II, Delhi 1950, pages 308–309; the book entitled "Indian Materia Medica" by Doctor K. M. Nadkarni's, third edition revised and enlarged by A. K. Nadkarni in two volumes, volume I, page 372; and the book entitled "The Flora of British India" by Sir J. D. Hooker, C. B., K. C., S. I., volume IV entitled "Asclepiadae to Amarantaceae", pages 624 to 627.

The use of *Coleus forskholii* as a raw material for the extraction of forskolin is already known, especially from the document FR-A-2 336 138. Forskolin is also known to have a slimming activity from a publication by GREENWAY in EP 190 165.

The documents FR-A-2 336 138 and EP-A1-0 243 646 also describe a number of pharmacological properties of these substances, such as a hypotensive and calming activity on the central nervous system.

The present invention is based on the discovery that extracts of *Coleus esquirolii, Coleus scutellarioides* or *Coleus xanthanthus*, although not containing forskolin, have valuable biological properties which can be used in the cosmetic and pharmaceutical fields. In particular, the inventors have observed that these extracts unexpectedly possess a melanogenesis-stimulating activity on the melanocytes present in the skin or the hair follicles, and thus make it possible to promote the pigmentation of the skin or hair as well as to treat pigmentation disorders of the skin and hair, more particularly by promoting the biosynthesis of melanin.

One object of the present invention is therefore to solve the new technical problem which consists in providing a novel cosmetic or pharmaceutical composition, especially dermatological composition, intended in particular for promoting the pigmentation of the skin or hair.

A further object of the present invention is to solve the new technical problem which consists in preparing a novel formulation of a cosmetic or pharmaceutical composition having a good melanogenesis-stimulating activity on the melanocytes present in the skin or the hair follicles.

A further object of the present invention is to provide a solution to the new technical problem which consists in providing a particularly easily obtainable plant extract which in itself has a good melanogenesis-stimulating activity on the melanocytes present in the skin or the hair follicles, without having to isolate an active substance of any kind, these isolation processes generally being lengthy and expensive.

All these new technical problems are solved for the first time by the present invention in a satisfactory manner which can be used on the industrial scale.

Thus, according to a first feature, the present invention relates to a cosmetic or pharmaceutical composition, especially dermatological composition, which comprises, as the active ingredient, an extract of *Coleus esquirolii, Coleus scutellarioides* or *Coleus xanthanthus,* or a mixture thereof.

According to a second feature closely related to the first feature, the present invention relates to a cosmetic or pharmaceutical composition, especially dermatological composition, intended for promoting the pigmentation of the skin or hair, said composition comprising, as the active ingredient, an extract of *Coleus esquirolii, Coleus scutellarioides* or *Coleus xanthanthus,* or a mixture thereof.

According to another characteristic, an organic extract of *Coleus esquirolii, Coleus scutellarioides* or *Coleus xanthanthus* is used which is found especially in India. This extract is advantageously obtained by a process comprising at least one extraction step with a solvent selected from the group consisting of ethyl acetate, methanol, ethanol and dichloromethane. In general, solvents which can be used are organic solvents such as aromatic hydrocarbons, halogenated aliphatic or aromatic hydrocarbons, dialkyl ethers, dialkyl ketones, alkanols, carboxylic acids and esters thereof, or other solvents like dimethylformamide, dioxane, tetrahydrofuran and dimethyl sulfoxide. Preferred solvents among those mentioned above are benzene, toluene or xylene, methylene chloride, chloroform, ethyl acetate, methanol or ethanol. The ratio of plant material to extraction agent is not critical and will generally be between 1:5 and 1:20 parts by weight, preferably about 1:10. The extraction is carried out at temperatures between room temperature and the boiling point of the solvent used for the extraction. An advantageous extraction technique is the so-called Soxhlet extraction technique. It may be advantageous, and in certain cases necessary, to evaporate the solvent off, for example by lyophilization, and to take up the crude extracts for the purpose of purification. Within the framework of the present invention, alcoholic extraction is particularly valuable, especially at the end of the procedure for obtaining the extract, because of the fact that alcohols usually have a low toxicity, a particularly advantageous alcohol being ethanol.

Another particularly advantageous solvent is ethyl acetate because it yields an extract of good efficacy.

In general, the concentration of the extracts used according to the present invention for the preparation of a cosmetic or pharmaceutical composition, expressed by dry weight, is between 0.001% and 2% by weight, preferably between 0.01% and 0.5% by weight, based on the total weight of the composition.

The cosmetic or pharmaceutical compositions, especially dermatological compositions, according to the present invention can be applied topically to promote the pigmentation of the skin and hair, in particular in compositions presented in the form of creams, gels or lotions and intended for application to the skin or hair.

Thus the cosmetic or pharmaceutical compositions, especially dermatological compositions, according to the invention have various applications in cosmetology or dermatology, in particular when it is desired to increase the pigmentation. For example, these compositions can be used as sun products for accelerating or intensifying tanning, which, in addition to the esthetic advantage often sought after, makes it possible to strengthen the natural defenses against ultraviolet radiation by increasing the melanin content of the epidermis. These compositions can also be used in the form of creams, for example, to give the skin a more sunburnt appearance, or else in the form of lotions in order to prevent and treat the appearance of gray hair. Furthermore, in dermatology, the compositions according to the present invention can be used as therapeutic agents, either by themselves or in association with other drugs, in particular by topical application in the treatment of melanogenesis dysfunctions.

In one advantageous embodiment, a cosmetic or pharmaceutical composition according to the invention also contains a xanthine, in particular IBMX or theophylline, preferably at a concentration by weight of between 0.01% and 2% and particularly preferably of between 0.01% and 0.5%, based on the total weight of the composition.

In another embodiment, a cosmetic or pharmaceutical composition according to the invention also contains tyrosine or a derivative thereof, preferably at a concentration by weight of between 0.001% and 10%, based on the total weight of the composition.

In yet another embodiment, a cosmetic or pharmaceutical composition according to the invention also contains an effective concentration of at least one other active substance selected from vitamins, in particular the B vitamins, quinine or derivatives thereof, rubefacients such as methyl nicotinate, a papilla fibroblast culture supernatant as defined in the document EP-A-272 920, keratin hydrolyzates, trace elements such as zinc, selenium and copper, 5-α-reductase inhibitors such as progesterone, cyproterone acetate and minoxidil, azelaic acid and derivatives thereof, a 4-methyl-4-azasteroid, in particular 17-β-N,N-diethyl-carbamoyl-4-methyl-4-aza-5-α-androstan-3-one, or else an extract of Serenoa repens.

According to a third feature, the present invention further relates to a process for the manufacture of a cosmetic or pharmaceutical composition, especially dermatological composition, intended in particular for promoting the pigmentation of the skin or hair, said process comprising the incorporation of at least one extract of *Coleus esquirolii, Coleus scutellarioides* or *Coleus xanthanthus,* or a mixture thereof, as described above, into a cosmetically or pharmaceutically acceptable excipient, vehicle or carrier.

According to a fourth feature, the invention relates to the use of an extract of *Coleus esquirolii, Coleus scutellarioides* or *Coleus xanthanthus,* or a mixture thereof, for the preparation of a cosmetic or pharmaceutical composition, especially dermatological composition, intended in particular for promoting the pigmentation of the skin or hair and/or for treating pigmentation disorders of the skin and hair.

Finally, according to a last feature, the present invention further relates to a method of treating the skin or hair in order to promote the pigmentation, said method comprising the application, in an amount effective for achieving pigmentation, of at least one extract of *Coleus esquirolii, Coleus scutellarioides* or *Coleus xanthanthus,* or a mixture thereof, as described above, incorporated in a cosmetically or pharmaceutically acceptable excipient, vehicle or carrier.

In all the foregoing features of the present invention, the abovementioned extract of Coleus can be incorporated into hydrated lipidic lamellar phases or into liposomes.

The term "lipidic" in the expression "lipidic lamellar phase" covers all substances which comprise a so-called fatty hydrocarbon chain generally containing more than 5 carbon atoms, this substance usually being called a "lipid".

According to the invention, the lipids used to form the lipidic lamellar phases or the liposomes are amphiphilic lipids, i.e. lipids consisting of molecular which possess either an ionic or a non-ionic hydrophilic group and a lipophilic group, these amphiphilic lipids being capable of forming lipidic lamellar phases or liposomes in the presence of an aqueous phase, depending on the amount of water in the mixture.

The following may be mentioned in particular among these lipids: phospholipids, phosphoaminolipids, glycolipids, polyoxyethylenated fatty alcohols and optionally polyoxyethylenated polyol esters. Such substances consist for example of an egg or soya lecithin, a phosphatidylserine, a sphyngomyelin, a cerebroside or an oxyethylenated polyglycerol stearate.

It is preferable according to the invention to use a mixture of lipids consisting of at least one amphiphilic lipid and at least one hydrophobic lipid such as a sterol like cholesterol or β-sitosterol. The amount of hydrophobic lipid, expressed in mol, must not generally exceed the amount of amphiphilic lipid and preferably must not be more than 0.5 times this amount.

The compounds or the extracts containing these compounds used according to the present invention can be incorporated into hydrated lipidic lamellar phases or into liposomes by known preparative techniques described for example in the document EP-B1-0 087 993, if appropriate in combination with the document EP-B1-0 107 559.

Other objects, characteristics and advantages of the invention will become clearly apparent from the following explanatory description referring to several Examples, which are given simply by way of illustration and which cannot therefore in any way limit the scope of the invention.

The percentages are given by weight in the Examples, unless indicated otherwise.

EXAMPLE 1

Preparation of an Extract of Coleus from *Coleus Esquirolii*

500 g of whole *Coleus esquirolii* plants are treated by the Soxhlet extraction technique with a sufficient amount of methanol to completely immerse the plant, for 3 h under reflux.

The methanolic extracts are filtered and the methanolic filtrate is evaporated under reduced pressure to give an extract of *Coleus esquirolii* called extract $I_1$.

EXAMPLE 2

An extract of *Coleus scutellarioides* called extract $I_2$ is obtained by following the procedure described in Example 1, except that the plant used is *Coleus scutellarioides* and the solvent used is ethyl acetate.

EXAMPLE 3

Preparation of an Extract of *Coleus Xanthanthus*

The procedure described in Example 1 is followed, except that the plant used is *Coleus xanthanthus,* the solvent still being methanol.

This gives an extract of *Coleus xanthanthus* called extract $I_3$.

EXAMPLE 4

Dried and finely ground roots of *Coleus esquirolii* (1 kg) are extracted in several stages with benzene (3×5 l), preferably by the Soxhlet extraction technique at 70° C. for several hours. The benzene extracts obtained are filtered and concentrated under vacuum to remove the benzene.

EXAMPLE 5

Incorporation of an Extract of *Coleus Esquirolii* into Hydrated Lipidic Lamellar Phases or into Liposomes An extract of *Coleus esquirolii* obtained according to Example 1 is incorporated into hydrated lipidic lamellar phases or into liposomes by the preparative technique below:

The following are weighed out:
—soya lecithin: 0.9 g
—β-sitosterol: 0.1 g
—lyophilized extract of Coleus $I_1$ of Example 1: 0.025 g These constituents are dissolved in a mixture consisting of 100 ml of dichloromethane and 25 ml of methanol.

The resulting mixture is evaporated on a rotary evaporator at a temperature of 45° C. under reduced pressure.

The resulting lipidic film is then taken up and dispersed in distilled water qsp 50 g at room temperature for 2 h, with agitation.

The suspension of lipidic vesicles obtained is then homogenized by treatment with ultrasound for 30 min at 4° C. with a power of 150W.

The mean size of the liposomes obtained in this way is about 212 nm.

In one advantageous variant, this suspension is then gelled by being mixed with 50 g of 1.25% Carbopol® 904 gel, separately prepared in conventional manner. This gives about 100 g of a gelled suspension of liposomes encapsulating the extract of *Coleus esquirolii*, the concentration of which is about 0,025%, based on the total weight of the suspension.

EXAMPLE 6

Measurement of the Activity of an Extract of *Coleus Esquirolii*, *Coleus Scutellarioides* or *Coleus Xanthanthus* According to the Invention on Melanocytes in Culture Protocol:

Murine melanocytes are cultivated on an appropriate medium in conventional manner.

On day D= 0, the test product is introduced into the culture medium.

On day D= 5, the cells are removed and isolated by centrifugation and the cellular residue is recovered and dissolved in 0.5N sodium hydroxide solution.

The optical density is read on a spectrophotometer at 475 nm, making it possible to evaluate the amount of melanin formed by comparison with the optical density of a solution of melanin of known concentration.

The cells are also counted and the amount of melanin formed per cell is calculated relative to a control culture, without the addition of test product.

Each extract of *Coleus esquirolii*, *Coleus scutellarioides* or *Coleus xanthanthus* was tested, at various concentrations in μg/ml, using as positive control a culture receiving β-MSH (MELANIN STIMULATING HORMONE) at a concentration of $2.10^{-8}M$.

The melanogenesis-stimulating activity A of the products according to the invention is calculated by means of the following formula:

$$A = \frac{q_p - q_o}{q_+ - q_o} \times 100$$

in which the quantities q represent the amounts of melanin formed:
$q_p$= culture receiving the test product
$q_+$= culture receiving β-MSH
$q_o$= control culture receiving no product The activity of these extracts, calculated according to the above formula, is shown in Tables I to III below for *Coleus esquirolii*, *Coleus scutellarioides* and *Coleus xanthanthus* respectively.

TABLE I

Extract of *Coleus esquirolii* (Example 1)

| Concentration of product, μg/ml | Numbers of cells per dish × 10³ | Melanin, μg per 10⁶ cells | Activity % | t |
|---|---|---|---|---|
| Control (no product) | 169 ± 5 | 68 ± 4 | 0 | |
| β-MSH at $2.10^{-8}M$ | 164 ± 5 | 136 ± 6 | 100 | |
| 2.5 | 159 ± 10 | 80 ± 4 | +18 | S |
| 5 | 164 ± 6 | 84 ± 3 | +23 | S |
| 10 | 156 ± 10 | 91 ± 3 | +34 | S |
| 25 | 155 ± 5 | 98 ± 8 | +44 | S |

TABLE II

Extract of *Coleus scutellarioides* (Example 2)

| Concentration μg/ml | Numbers of μg/ml of dishes × 10³ | Melanin, μg per 10⁶ cells | Activity % | t |
|---|---|---|---|---|
| Control (no product) | 161 ± 11 | 68 ± 6 | 0 | |
| β-MSH at $2.10^{-8}M$ | 158 ± 7 | 138 ± 4 | 100 | |
| 2.5 | 166 ± 14 | 88 ± 5 | +28 | S |
| 5 | 161 ± 4 | 96 ± 3 | +40 | S |
| 10 | 159 ± 2 | 108 ± 2 | +57 | S |
| 25 | 183 ± 2 | 63 ± 3 | −7 | NS |

TABLE III

Extract of *Coleus xanthanthus* (Example 3)

| Concentration of product, μg/ml | Numbers of cells per dish × 10³ | Melanin, μg per 10⁶ cells | Activity % | t |
|---|---|---|---|---|
| Control (no product) | 167 ± 7 | 45 ± 1 | 0 | |
| β-MSH at $2.10^{-8}M$ | 162 ± 4 | 121 ± 1 | 100 | |
| 0.25 | 162 ± 13 | 51 ± 3 | +8 | NS |
| 1 | 149 ± 8 | 54 ± 3 | +12 | S |
| 2.5 | 162 ± 22 | 54 ± 4 | +12 | S |
| 10 | 165 ± 10 | 56 ± 4 | +14 | S |

TABLE III-continued

Extract of *Coleus xanthanthus* (Example 3)

| Concentration of product, μg/ml | Numbers of cells per dish × 10³ | Melanin, μg per 10⁶ cells | Activity % | t |
|---|---|---|---|---|
| 25 | 176 ± 3 | 54 ± 3 | +12 | S |

Tables I to III above show that the extracts of Coleus according to the invention stimulate the production of melanin to a significant extent, representing a totally unexpected result for those skilled in the art.

Various Examples of the formulation of a cosmetic or pharmaceutical composition, especially dermatological composition, active in the treatment of skin pigmentation disorders, are now given below.

EXAMPLE 7

Face Tanning Gel

| | |
|---|---|
| Extract of Coleus (dry weight) according to Example 1 | 0.035 g |
| Ethanol | 40.— g |
| Distilled water | 20.— g |
| 1% Carbopol ® 940 gel | qsp 100 g |

EXAMPLE 8

Tanning Sun Cream

| | |
|---|---|
| Extract of Coleus (dry weight) according to Example 2 | 0.03 g |
| Isocetyl stearate | 8.— g |
| Hydrogenated groundnut oil | 10.— g |
| Lanolin oil | 3.5 g |
| Cetyl alcohol | 5.— g |
| Stearyl alcohol | 2.5 g |
| Light liquid petrolatum | 10.— g |
| Neutralized phosphoric acid monoester of EO cetyl alcohol | 3.— g |
| Octyl methoxycinnamate | 5.— g |

This phase is emulsified with an aqueous phase qsp 100 g containing:

| | |
|---|---|
| Pantothenol | 0.1 g |
| Preservatives | 0.2 g |

EXAMPLE 9

Lotion for Strengthening the Natural Solar Protection

| | |
|---|---|
| Alcohol | 42.5 g |
| Propylene glycol | 3.— g |
| Menthol | 0.05 g |
| Hydroxypropyl methyl cellulose | 1.5 g |
| Extract of Coleus (dry weight) according to Example 2 | 0.03 g |
| Perfumed aqueous excipients | qsp 100 g |

This lotion is applied locally, preferably twice a day for 3 to 8 days preceding prolonged exposure to the sun. Daily applications can be continued during the period of exposure.

EXAMPLE 10

Hair Tonic Lotion for Combating Gray Hair

| | |
|---|---|
| Extract of Coleus according to Example 3 | 0.02 g |
| IBMX | 0.1 g |
| Alcohol | 30.— g |
| Water | 69.— g |
| Perfumed excipients | qsp 100 g |

This lotion can be applied to the hair and scalp twice a day in three-month courses of treatment.

EXAMPLE 11

Dermatological Gel Intended for Promoting the Pigmentation of the Skin

| | |
|---|---|
| Extract of Coleus according to Example 3 | 0.03 g |
| Ethanol | 30 g |
| Distilled water | 20 g |
| Carbopol ® gel | qsp 100 g |

This gel is used once or twice a day by local application to the areas of skin to be treated.

EXAMPLE 12

Hair Lotion for Combating Gray Hair

| | |
|---|---|
| Extract of Coleus according to Example 1 | 0.03 g |
| L-Tyrosine ethyl ester.HCl | 1.0 g |
| Ethanol | 40.0 g |
| Perfume | 0.5 g |
| Perfume solubilizer | 0.2 g |
| Water | qsp 100 g |

This lotion, applied daily to the hair and scalp, makes it possible to delay the appearance of gray hair.

EXAMPLE 13

Tanning Gel

| | |
|---|---|
| Extract of Coleus according to Example 1 | 0.02 g |
| Sun filter (EUSOLEX 232 TS ®) | 8.0 g |
| Ethanol | 40.0 g |
| Carbopol 940 ® | 1.0 g |
| Water | qsp 100 g |

EXAMPLE 14

Lotion for Preventing the Appearance of Gray Hair

| | |
|---|---|
| Liposome suspension according to Example 5 | 50 g |
| Carbopol 940 ® | 0.05 g |
| Glucose tyrosinate | 0.05 g |
| Trace element complex | 0.1 g |
| Theophylline | 0.01 g |
| Preservative | 0.05 g |
| Distilled water | qsp 100 ml |

This solution is applied in the evening to the graying areas of the scalp in a 4-month course of treatment.

Of course, the invention includes all means which constitute technical equivalents of the means described, as well as the various combinations thereof.

What is claimed is:

1. A method of treating the skin or hair to promote pigmentation thereof comprising applying to said skin or hair to be pigmented, an effective amount of a Coleus extract selected from the group consisting of an extract of *Coleus esquirolii*, an extract of *Coleus scutellarioides*, an extract of *Coleus xanthantus*, and any mixture thereof.

2. The method of claim 1, wherein said Coleus extract is incorporated in a cosmetically or pharmaceutically acceptable excipient, vehicle or carrier.

3. The method of claim 1, wherein said Coleus extract is incorporated in a lipidic component selected from hydrated lipidic lamellar phases and liposomes.

4. The method of claim 1, wherein said Coleus extract is an organic extract obtained by a process comprising at least one extraction step with an organic solvent selected from the group consisting of ethyl acetate, methanol, ethanol and dicholoromethane.

5. The method of claim 1, wherein said coleus extract is present in a composition which further comprises a further active substance selected from the group consisting of a xanthine, tyrosine, a tyrosine derivative, a vitamin, quinine, a quinine derivative, a rubefacient, a 5-α-reductase inhibitor, azelaic acid, an azelaic acid derivative, a 4-methyl-4-azasteroid, and an extract of Serenoa repens.

6. The method of claim 5, wherein said xanthine is selected from isobutylmethylxanthine and theophylline; said vitamin is vitamin B; said rubefacient is methyl nicotinate; said 5-α-reductase inhibitor is selected from the group consisting of progesterone, cyproterone acetate and minoxidil; said 4-methyl-4-azasteroid is 17-β-N,N-diethylcarbamoyl-4-methyl-4-aza-5-α-androstan-3-one.

7. The method of claim 1, wherein said Coleus extract is present in a composition for topical application.

8. The method of claim 7, wherein said composition is selected from the group consisting of a cream, a gel and a lotion.

9. The method of claim 1, wherein said Coleus extract is present in a composition having a concentration in Coleus extract, expressed in dry weight, ranging between 0.001% and 2% by weight based on the total weight of the composition.

10. The method of claim 9, wherein said Coleus extract is ranging between 0.01% and 0.5% by weight based on the total weight of the composition.

11. The method of claim 5, wherein said xanthine is present in a concentration by weight ranging between 0.01 and 2% based on the total weight of the composition.

12. The method of claim 5, wherein said tyrosine and said tyrosine derivative are independently present in the composition at the concentration by weight ranging between 0.001% and 10% based on the total weight of the composition.

13. The method of claim 1, wherein said method is a method for treating melanogenesis disfunctions of the skin or hair.

14. A composition selected from a cosmetic and a pharmaceutical composition, comprising as active ingredient a Coleus extract selected from the group consisting of an extract of *Coleus esquirolii*, an extract of *Coleus scutellarioides*, an extract of *Coleus xanthantus* and any mixture thereof.

15. The composition of claim 14, wherein said Coleus extract is an organic extract of Coleus obtained by a process comprising at least one extraction step with an organic solvent selected from the group consisting of ethyl acetate, methanol, ethanol and a dichloromethane.

16. The composition of claim 14, wherein the concentration of the Coleus extract, expressed by dry weight, ranges between 0.001% and 2% by weight, based on the total weight of the composition.

17. The composition of claim 16, wherein the concentration of the Coleus extract ranges between 0.01% and 0.5% by weight based on the total weight of the composition.

18. The composition of claim 14, wherein the composition further contains a xanthine at a concentration by weight ranging between 0.01 and 2% based on the total weight of the composition.

19. The composition of claim 18, wherein said xanthine is selected from isobutylmethylxanthine and theophylline.

20. The composition of claim 14, wherein said composition further comprises a tyrosine component selected from tyrosine and a tyrosine derivative, at a concentration by weight ranging between 0.01% and 10% based on the total weight of the composition.

21. The composition of claim 14, further comprising an active substance selected from the group consisting of a xanthine, tyrosine, a tyrosine derivative, a vitamin, quinine, a quinine derivative, a rubefacient, a 5-α-reductase inhibitor, azelaic acid, an azelaic acid derivative, a 4-methyl-4-azasteroid, and an extract of Serenoa repens.

22. The composition of claim 14, wherein said composition is for topical application.

23. The composition of claim 22, wherein said composition is selected from the group consisting of a cream, a gel and a lotion.

* * * * *